United States Patent [19]
Torimae et al.

[11] Patent Number: 5,849,001
[45] Date of Patent: Dec. 15, 1998

[54] POROUS SHEET AND ABSORBENT ARTICLE USING THE SAME

[75] Inventors: Yasuhiro Torimae; Tetsuji Kitoh; Takahiro Sato, all of Wakayama, Japan

[73] Assignee: Kao Corporation, Tokyo, Japan

[21] Appl. No.: 596,401

[22] Filed: Feb. 2, 1996

[30] Foreign Application Priority Data

Feb. 2, 1995 [JP] Japan .................................. 7-016300
Aug. 25, 1995 [JP] Japan .................................. 7-217841

[51] Int. Cl.$^6$ ...................................................... A61F 13/15
[52] U.S. Cl. ........................ 604/372; 604/367; 428/315.5; 428/315.7
[58] Field of Search ..................................... 604/358, 367, 604/370, 372, 385.1; 428/315.5, 315.7

[56] References Cited

U.S. PATENT DOCUMENTS

| | | |
|---|---|---|
| 4,539,256 | 9/1985 | Shipman . |
| 4,726,989 | 2/1988 | Mrozinski . |
| 4,957,943 | 9/1990 | McAllister ........................... 428/315.5 |

FOREIGN PATENT DOCUMENTS

| | | |
|---|---|---|
| 63-161035 | 7/1988 | Japan . |
| 598057 | 4/1993 | Japan . |
| 5-38011 | 6/1993 | Japan . |

OTHER PUBLICATIONS

English language abstract of Japanese Patent Application Laid–Open No. 5–98057.

*Primary Examiner*—Robert A. Clarke
*Attorney, Agent, or Firm*—Birch, Stewart, Kolasch & Birch, LLP

[57] ABSTRACT

The porous sheet obtainable by stretching, in at least one direction, a sheet formed from a melt mixture of a resin composition comprising:

100 parts by weight of a resin mixture consisting of 63 to 90 parts by weight of a crystalline polyolefin resin, and 37 to 10 parts by weight of a compound having a volatile temperature at an ambient pressure of 240° C. or higher and a melting temperature of 90° C. or lower; and 7 to 40 parts by weight of a particulate material having an average particle diameter of 0.3 to 8 μm and a maximum particle diameter of 13 μm or smaller, the particulate material being not melted at the molding temperature of the resin mixture is disclosed.

15 Claims, 1 Drawing Sheet

FIG.1

POROUS SHEET AND ABSORBENT ARTICLE USING THE SAME

BACKGROUND OF THE INVENTION

1. Field of the Invention

This invention relates to a porous sheet and an absorbent article using the porous sheet. This invention particularly relates to a porous sheet, which has a high tensile strength, good molding productivity, a high moisture permeability, and a high water pressure resistance, and an absorbent article using the porous sheet.

2. Description of the Related Art

As one of processes for producing porous sheets, a process has heretofore been known, wherein an olefin resin, such as polyethylene or polypropylene, is melted and kneaded together with at least 40 parts by weight of an inorganic filler, a sheet is formed from the melt mixture, and the sheet is then stretched in one direction or in two directions. The porous sheets obtained in this manner have good air permeability and good moisture permeability and are free of a moisture condensation phenomenon. Therefore, the porous sheets are used as decorative sheets for the walls of rooms, packaging sheets, and the like.

Also, in cases where the porous sheets having the good properties as described above are further imparted with softness, the porous sheets can be used as backsheets of absorbent articles, such as disposable diapers. In order for the porous sheets to be imparted with softness, for example, a technique has heretofore been proposed, wherein a linear low-density polyethylene is utilized as the olefin resin.

Popular disposable diapers comprise an absorbent member for absorbing discharged liquids, such as urine, a topsheet which covers the top surface of the absorbent member and which, in use, contacts the skin of the wearer, and a backsheet which covers the back surface of the absorbent member and prevents liquid leakage. The absorbent member, the topsheet, and the backsheet are adhered together into an integral body. The disposable diapers are also provided with expansion-contraction functions, which prevent liquid leakage from the waist corresponding portion and the leg corresponding portion of the diaper, and a securing function constituted of tapes, or the like, for securing the back-side waist corresponding portion and the abdomen-side waist corresponding portion to each other when the diaper is put on the wearer. For convenience, securing tapes having a width of approximately 25 mm is used popularly. However, the problems occur in that, when the securing tapes are released for the purposes of correcting the wearing condition of the diaper, investigating the urine discharge in use of the diaper, or the like, the backsheet formed from the aforesaid porous sheet having been imparted with softness breaks due to its insufficient strength, and therefore the diaper must be exchanged with a new one.

In order to eliminate the problems described above, a wide holding tape, which is ordinarily referred to as the landing tape, is sealed to the backsheet at the abdomen-side waist corresponding portion of the diaper. When the diaper is put on the wearer, the securing tape, which is ordinarily referred to as the fastening tape, is adhered to the landing tape. In such cases, the securing tape can be repeatedly adhered to and released from the landing tape.

However, the use of the landing tape has the drawbacks in that (1) the number of the diaper constituting members and the number of the production steps cannot be kept small, (2) the landing tape is most expensive among the diaper materials, and therefore the use of the wide landing tape (i.e., a large amount of the landing tape) leads to an increase in the cost of the diaper, and (3) even if the landing tape having the large width is used, the fastening tape will often adhere to a portion of the backsheet other than the landing tape, depending on the form of the body of the wearer, and the adhering and release of the fastening tape cannot be carried out repeatedly.

Accordingly, a porous sheet having an enhanced strength is proposed in, for example, Japanese Unexamined Patent Publication No. 5(1993)-98057. The proposed porous sheet is obtained with a process, wherein a specific polyolefin, a filler, a specific plasticizing agent, and a radical forming agent are mixed together, the resulting mixture is subjected to an inflation molding step, and the resulting sheet is stretched in one direction along the take-off direction. The proposed porous sheet has a strength a little less than two times as large as the strength of a porous sheet, which is obtained by stretching a sheet formed from a melt mixture of an ordinary olefin resin and an inorganic filler. However, with the porous sheet having the strength of this level, the landing tape of the disposable diaper, or the like, cannot be omitted.

Further, since a radical forming agent is used, the melt flow characteristics of the molded product becomes different from the melt flow characteristics of the composition before being molded. Therefore, problems occur in that it is difficult for the unnecessary portions, such as edge portions, occurring in the ordinary actual production steps to be processed for recycling, and the productivity cannot be kept high.

Also, for example, in Japanese Patent Publication No. 5(1993)-38011, a microporous sheet is proposed which is obtained with a process for producing a microporous sheet, wherein a specific crystalline polymer and a specific compound compatible with the polymer are melted and blended together, a sheet is formed from the resulting mixture, phase separation is caused to occur in the sheet during a cooling step, and the sheet is then stretched. The proposed microporous sheet has a strength two to three times as large as the strength of a porous sheet, which is obtained by stretching a sheet formed from a melt mixture of an ordinary olefin resin and an inorganic filler. However, even with the microporous sheet having the strength of this level, the landing tape of the disposable diaper, or the like, cannot be omitted. Research carried out by the inventors revealed that, in order for the landing tape of the disposable diaper, or the like, to be omitted, it is necessary for the porous sheet to have a strength at least four times, preferably five times, as large as the strength of the porous sheet obtainable with the ordinary production process.

Further, one of the most detrimental defects of the microporous sheet described above is that the antileakage characteristics are low. Specifically, the antileakage characteristics required for the antileakage sheets of diapers, or the like, are at least one hour. However, with the microporous sheet described above, urine leakage occurs within 30 minutes even at a water pressure resistance of zero (atmospheric pressure). The antileakage characteristics become bad particularly when a liquid compound is employed as the specific compound compatible with the polymer described above. However, in order for a feeling (i.e., softness) required for diapers, or the like, to be obtained, it is preferable that the liquid compound is employed. In view of the above, such a microporous sheet is unsuitable for use in diapers, or the like. This can also be understood from the fact that, when the conventional system of the polyethylene resin and the filler (primarily $CaCO_3$) and the system of the polypropylene resin and the specific compound compatible with the polymer (primarily a mineral oil) in the sheet composition described above (i.e., the aforesaid microporous sheet) are compared with each other, the respective materials in the latter system are more hydrophobic than the materials in the former system, but the waterproofness of the latter system is rated to be lower than the waterproofness of the former system.

Further, for example, Japanese Unexamined Patent Publication No. 63(1988)-161035 discloses specific compounds as crystal nucleating agents to be used in producing the sheet described above. The disclosed specific compounds include those which do not melt at the molding temperature. However, the disclosed specific compounds do not suggest an improvement in the stretching pore-forming characteristics.

SUMMARY OF THE INVENTION

The primary object of the present invention is to provide a porous sheet, which has a high air permeability, a high moisture permeability, good antileakage characteristics, good feeling, and a high strength (a high tearing strength and a high tensile strength at yield point), and which is capable of being produced industrially and continuously with a high productivity in a safe and quick manner.

Another object of the present invention is to provide an absorbent article using the porous sheet.

The inventors carried out intensive research to solve the problems described above and found that the objects can be accomplished with a porous sheet formed from a melt mixture of a resin composition comprising, in specific blending proportions, a crystalline polyolefin resin, a compound having a specific volatile temperature and a specific melting temperature, and a particulate material having a specific particle diameter.

The present invention is based on such findings. Specifically, the present invention provides a porous sheet obtainable by stretching, in at least one direction, a sheet formed from a melt mixture of a resin composition comprising:

100 parts by weight of a resin mixture consisting of 63 to 90 parts by weight of a crystalline polyolefin resin, and 37 to 10 parts by weight of a compound having a volatile temperature at an ambient pressure of 240° C. or higher and a melting temperature of 90° C. or lower; and 7 to 40 parts by weight of a particulate material having an average particle diameter of 0.3 to 8 $\mu$m and a maximum particle diameter of 13 $\mu$m or smaller, the particulate material being not melted at the molding temperature of the resin mixture.

The present invention also provides an absorbent article comprising a liquid permeable topsheet, an antileakage backsheet, and an absorbent member interposed between the topsheet and the backsheet, characterized in that the backsheet comprises the porous sheet in accordance with the present invention.

The porous sheet in accordance with the present invention has a high air permeability, a high moisture permeability, and good antileakage characteristics. Also, the porous sheet in accordance with the present invention has good feeling and a high strength (a high tearing strength and a high tensile strength at yield point). The porous sheet in accordance with the present invention is capable of being produced industrially and continuously with a high productivity in a safe and quick manner.

Further, the porous sheet in accordance with the present invention has a high air permeability, a high moisture permeability, a high water resistance, good feeling, and a high strength, and is capable of being produced industrially and continuously with a high productivity in a safe and quick manner.

With the absorbent article in accordance with the present invention, even if a landing tape is not used, the adhering and release of a fastening tape can be carried out repeatedly. Therefore, the absorbent article in accordance with the present invention has good serviceability and is advantageous from the view-point of economy.

DETAILED DESCRIPTION OF THE INVENTION

The porous sheet in accordance with the present invention will be described hereinbelow.

The porous sheet in accordance with the present invention is obtained by stretching the sheet formed from the melt mixture of the resin composition comprising the resin mixture and the specific particulate material. The resin mixture consists of the crystalline polyolefin resin and the specific compound in the specific blending proportions.

Examples of the crystalline polyolefin resins employed in the resin composition in the porous sheet in accordance with the present invention include a polypropylene resin, an ethylene-propylene block copolymer resin, and a mixture of the ethylene-propylene block copolymer resin and a polypropylene resin and/or a polyethylene resin. Examples of the polypropylene resins include an isotactic polypropylene resin and a syndiotactic polypropylene resin.

Specifically, as the crystalline polyolefin resin capable of being used in the present invention, the resins described in items (1) through (5) below may be mentioned.

(1) A polypropylene resin (2) The block copolymer resin described above (3) A mixture of the block copolymer resin described above and a polypropylene resin (4) A mixture of the block copolymer resin described above and a polyethylene resin (5) A mixture of the block copolymer resin described above, a polypropylene resin, and a polyethylene resin As the polypropylene resin used in (3) and (5) above, the isotactic polypropylene resin is preferable.

The melt indices of the aforesaid block copolymer resin, the aforesaid propylene resin, and the aforesaid polyethylene resin, which may be used as the crystalline polyolefin resin described above, should preferably be at most 3 g/10 minutes, should more preferably be 0.2 to 3 g/10 minutes, and should most preferably be 0.2 to 2 g/10 minutes.

If the melt index of each of the resins described above is larger than 3 g/10 minutes, the tearing strength and the tensile strength of the obtained porous sheet will become low, and it will be difficult for the strength required for backsheets of absorbent articles, such as disposable diapers, to be obtained. Also, in such cases, in order that the desired level of the strength may be obtained, the thickness of the porous sheet may be increased. However, if the thickness of the porous sheet is increased, the moisture permeability will become low, and the cost of the product will become high.

If the melt index of each of the resins described above is smaller than 0.2 g/10 minutes, a large power will be required for the extrusion molding for forming the sheet, and the productivity will become low. Therefore, the above-mentioned range is preferred.

The term "melt index" as used herein means the value measured in accordance with ASTM D-1238 under the conditions of 230° C. and 2.16 kgf for the polypropylene resin and the block copolymer resin described above, and under the conditions of 190° C. and 2.16 kgf for the polyethylene resin.

In cases where the porous sheet in accordance with the present invention is used as the backsheet of an absorbent article, the porous sheet should have an appropriate feeling and an appropriate strength (i.e., an appropriate tearing strength and an appropriate tensile strength at yield point). For such purposes, the weight ratio, on the monomer basis, of ethylene to propylene (i.e. [% by weight of ethylene]/[% by weight of propylene]) in the crystalline polyolefin resin described above should preferably be between 4/96 and 40/60, and should more preferably be between 8/92 and 30/70. Two or more of the resins and the copolymer resins, i.e. the resins described in (1) through (5) above, may be used in combination such that the aforesaid weight ratio may fall within the range described above.

If the aforesaid weight ratio, on the monomer basis, is less than 4/96, the tearing strength will become low, and the feeling will become bad. If the aforesaid weight ratio, on the monomer basis, is more than 40/60, the sheet must be stretched at a high stretch ratio in order for the desired level of the moisture permeability to be obtained. If the sheet is stretched at such a high stretch ratio in order for the desired level of the moisture permeability to be obtained, the tearing strength will become low.

Also, if the crystalline polyolefin resin is a random copolymer, even though the weight ratio, on the monomer basis, of ethylene to propylene falls within the aforesaid preferable range, the desired level of the moisture permeability cannot easily be obtained, and the tearing strength and the tensile strength will low.

In the present invention, the aforesaid specific compound employed in the resin composition described above has a volatile temperature at an ambient pressure of 240° C. or higher. The specific compound should preferably have a volatile temperature at an ambient pressure of 250° C. or higher, and should more preferably have a volatile temperature at an ambient pressure of 260° C. or higher. Also, the specific compound has a melting temperature of 90° C. or lower. The specific compound should preferably have a melting temperature of 70° C. or lower, and should more preferably have a melting temperature of 50° C. or lower. (The specific compound will hereinbelow be simply referred to as "compound".)

In the present invention, the molding temperature, at which the melt mixture of the resin composition is molded to form the sheet, should preferably be 180° to 250° C., and should more preferably be 190° to 240° C. Therefore, if the volatile temper aforesaid compound at an ambient pressure is lower than 240° C., fuming of the volatile matter will be apt to occur during the molding step. If the fuming of the volatile matter occurs during the molding step, there will be the risk that environmental pollution and ignition occur. Further, the volatile matter stuck (so-called "gum in the eyes") to die lips causes scorching. Therefore, in cases where the fuming occurs, the problems occur in that the sheet molding operation must often be temporarily ceased in order to clean the die lips, and the industrial productivity becomes markedly low.

Also, as described above, the melting temperature of the aforesaid compound is limited to 90° C. or lower. This is because, if this compound is softened or melted at the stretching temperature in the step for stretching the molded sheet, the sheet can easily be imparted with the microporosity.

The term "volatile temperature" as used herein means the temperature, at which the weight loss found from a heating loss curve depicted by measuring the volatile weight loss with a thermobalance in a nitrogen stream (30 ml/min.) under the conditions of a temperature rise rate of 10° C./min. and a sample weight of 10 mg is 1%.

Also, the term "melting temperature" as used herein means the value as measured with the "rise melting temperature" according to Japan Oil and Fat Chemical Society test method code No. 2.3.4.2-90 described in "Standard Oil And Fats Analysis Test Methods (1990)" edited by Japan Oil and Fat Chemical Society. The melting temperature of a liquid compound, which flows at 0° C., is indicated as "0° C. or lower."

Examples of the aforesaid compounds include a mineral oil and a compound having an ester bond in the molecule thereof.

Examples of the mineral oils include naturally-originating aromatic/alicyclic/fatty hydrocarbons, from which the low volatile matters have been removed, and alicyclic/fatty hydrocarbons, which are obtained by removing the aromatic constituents with hydrogenation of these aromatic/alicyclic/fatty hydrocarbons. Ethylene/α-olefin oligomers, which are referred to as the synthetic mineral oils, may also be mentioned as the examples of the mineral oils.

Examples of the compounds having an ester bond in the molecules thereof include (i) ester compounds obtainable from dehydration condensation reactions of fatty or aromatic, monobasic or polybasic carboxylic acids and fatty, alicyclic, or aromatic, monohydric or polyhydric alcohols; and (ii) ester compounds (i.e., monoester or polyester compounds) obtainable from dehydration condensation reactions of compounds having both the hydroxyl group and the carboxyl group in the molecules thereof.

As the fatty carboxylic acids and the aromatic carboxylic acids, polybasic carboxylic acids are preferable. As the aromatic polybasic carboxylic acids, aromatic dicarboxylic acids, aromatic tricarboxylic acids, and aromatic tetracarboxylic acids are preferable. Examples of the preferable aromatic polybasic carboxylic acids include phthalic acid, trimellitic acid, and pyromellitic acid. As the fatty polybasic carboxylic acids, fatty dicarboxylic acids and fatty tricarboxylic acids are preferable. Examples of the preferable fatty polybasic carboxylic acids include adipic acid, sebacic acid, and citric acid.

As the alcohols, monohydric alkyl alcohols are preferable. Examples of the preferable alcohols include octyl alcohol, lauryl alcohol, stearyl alcohol, and oleyl alcohol.

The most preferred example of the compound having an ester bond in the molecule thereof includes an ester compound obtainable from a polyhydric alcohol and a monobasic carboxylic acid, in particular, an ester compound obtainable from trimethylolpropane and lauric acid.

In the present invention, the specific blending proportions of the aforesaid crystalline polyolefin resin and the aforesaid compound in the resin mixture employed in the aforesaid resin composition are such that the proportion of the crystalline polyolefin resin may fall within the range of 63 to 90 parts by weight, and the proportion of the aforesaid compound may fall within the range of 37 to 10 parts by weight. The blending proportions should preferably be such that the proportion of the crystalline polyolefin resin may fall within the range of 68 to 88 parts by weight, and the proportion of the aforesaid compound may fall within the range of 32 to 12 parts by weight. The blending proportions should more preferably be such that the proportion of the crystalline polyolefin resin may fall within the range of 73 to 85 parts by weight, and the proportion of the aforesaid compound may fall within the range of 27 to 15 parts by weight.

If the blending proportion of the aforesaid compound is higher than 37 parts by weight, the strength of the porous sheet obtained from the stretching step will become insufficient, and the waterproofness of the porous sheet will become low. In addition, the aforesaid compound will bleed out from the porous sheet during the long-period storage, and the service-ability of the porous sheet cannot be kept high. If the blending proportion of the aforesaid compound is lower than 10 parts by weight, a porous sheet having a desired level of the moisture permeability cannot be obtained from the stretching step.

In the present invention, the aforesaid particulate material contained together with the aforesaid resin mixture in the aforesaid resin composition is not melted at the molding temperature of the aforesaid resin mixture (i.e., at the sheet molding temperature).

The research carried out by the inventors revealed that, in cases where the aforesaid particulate material is added, the moisture permeability can be obtained with a lower stretch ratio, the decrease in the tensile stress at yield point due to the stretching (in the direction perpendicular to the stretching direction) is smaller, and a moisture permeable sheet having a higher strength can be obtained than when the particulate material is not added. It is presumed that, by the synergistic effects of the aforesaid particulate material and the aforesaid compound, the moisture permeability sufficient for use as, for example, the backsheet of an absorbent article can be obtained even with the low stretch ratio, which does not cause the tearing strength in the stretching direction to become low.

Examples of the aforesaid particulate materials include fillers which are ordinarily used in rubber, plastic materials, and the like, for example, calcium carbonate, gypsum, barium sulfate, talc, clay, silica, metal powder and other inorganic materials, and metal salts of organic materials which primarily consist of inorganic substances. Also, particulate or powder-like materials of thermosetting resins, such as a phenolic resin, an epoxy resin, and sodium polyacrylate can be used. Among the above-enumerated particulate materials, inorganic particulate materials are preferred with calcium carbonate being more preferred.

The aforesaid particulate material has an average particle diameter of 0.3 to 8 $\mu$m and a maximum particle diameter of 13 $\mu$m or smaller. The particulate material should preferably have an average particle diameter of 0.5 to 5 $\mu$m and a maximum particle diameter of 10 $\mu$m or smaller. The particulate material should more preferably have an average particle diameter of 0.7 to 3 $\mu$m and a maximum particle diameter of 7 $\mu$m or smaller.

If the average particle diameter of the aforesaid particulate material is larger than 8 $\mu$m, the tensile strength of the sheet will become low. If the average particle diameter of the aforesaid particulate material is smaller than 0.3 $\mu$m, the particulate material cannot substantially contribute to the stretching pore-forming characteristics. If the maximum particle diameter of the particulate material is larger than 13 $\mu$m, breakage of the sheet will frequently occur when the sheet is formed from the melt mixture and when the sheet is stretched.

Measurement of the particle size distribution in the present invention was carried out with a centrifugal sedimentation type of particle size distribution measuring machine (Model SA-CP2 supplied by Shimadzu Corp.) by adding a measurement sample to a 0.2 wt % solution of sodium hexametaphosphate and thereafter carrying out ultrasonic dispersing treatment.

The blending proportion of the aforesaid particulate material is 7 to 40 parts by weight per 100 parts by weight of the aforesaid resin mixture. The blending proportion of the particulate material should preferably be 10 to 35 parts by weight per 100 parts by weight of the aforesaid resin mixture, and should more preferably be 12 to 30 parts by weight per 100 parts by weight of the aforesaid resin mixture.

If the blending proportion of the aforesaid particulate material is lower than 7 parts by weight per 100 parts by weight of the aforesaid resin mixture, the stretching pore-forming characteristics will become low. If the blending proportion of the particulate material is higher than 40 parts by weight per 100 parts by weight of the aforesaid resin mixture, the tensile strength will become low.

If the particulate materials are melted at the molding temperature of the aforesaid resin mixture, it will become difficult to control to the required particle diameter in the molded sheet. Therefore, it is necessary that the particulate materials are not melted at the molding temperature of the aforesaid resin mixture. The melting temperature of the particulate materials may take any value such that they are not melted at the aforesaid molding temperature. However, the melting temperature of the particulate materials should preferably be 250° C. or higher, and should more preferably be 300° C. or higher.

A nucleating agent (i.e., a crystal nucleating agent) should preferably be added to the aforesaid resin composition. High rigidity, high cycle grades of crystalline polyolefin resins having been blended with nucleating agents are available commercially. Crystalline polyolefin resins, which have not been blended with nucleating agents but have been blended with substances substantially having the nucleating agent functions, are also available commercially. Several kinds of fillers and several kinds of pigments have such functions. In cases where use is made of the grades, which have not been blended with the nucleating agents or the substances substantially having the nucleating agent functions, or the grades, which have been blended with the nucleating agents or the substances substantially having the nucleating agent functions but have only small nucleating effects, a nucleating agent should preferably be added to the aforesaid resin composition. In such cases, no limitation is imposed on the kind of the nucleating agent used, and any of nucleating agents known in the art may be employed. For example, it is possible to use the nucleating agents described in the column entitled "Functions and Effects of Plastic Blending Agents; Nucleating Agents" in "Plastics" published by Kogyo Chosa-kai Publishing Co., Ltd., Vol. 43, No. 11, pp. 113–116. Examples of the nucleating agents include high-melting temperature polymer nucleating agents, such as metal salts of aromatic carboxylic acids [e.g., aluminum hydroxypara-t-butyl benzoate (Al-PTBBA)], sorbitol derivatives, and organic phosphates [e.g., 2,2-methylenebis (4,6-di-t-butylphenyl)phosphate (PTBNa)]; and inorganic nucleating agents, such as titanium oxide and talc.

When necessary, additives, such as stabilizing agents and coloring agents, may be added to the aforesaid resin composition. As the stabilizing agents and coloring agents, any of known agents may be used.

Also, when necessary, ordinary resin physical property improvers, such as antistatic agents, may be used as additives in small amounts, which do not adversely affect the basic physical properties of the porous sheet in accordance with the present invention.

In cases where these nucleating agents and additives are added to the resin composition, the proportions of the additives should preferably be 0.01% to 10% by weight with respect to the total amount of the resin composition, and should more preferably be 0.1% to 5% by weight with respect to the total amount of the resin composition.

The porous sheet in accordance with the present invention is obtainable by stretching, in at least one direction, the sheet molded from the melt mixture of the aforesaid resin composition.

The "molding" and the "stretching" will later be described in detail with reference to the explanation of the production process.

The moisture permeability of the porous sheet in accordance with the present invention should preferably be 0.5 to 4.0 g/[100 cm$^2$.Hr], and should more preferably be 1.0 to 2.5 g/[100 cm$^2$.Hr]. If the moisture permeability is lower than 0.5 g/[100 cm$^2$.Hr], the effects of preventing stuffiness will become low when the porous sheet is used as the backsheet of an absorbent article. If the moisture permeability is higher than 4.0 g/[100 cm$^2$.Hr], the water pressure resistance and the antileakage characteristics will become bad. Therefore, the above-mentioned range is preferred. Also, in cases where the porous sheet is used as the backsheet of an absorbent article, such as a disposable diaper, the water pressure resistance of the porous sheet should preferably be 1.5 mAq or higher, and should more preferably be 2.0 mAq or higher. The waterproofness of the porous sheet (as measured with the rating method described in examples below) should preferably be at least one hour, should more preferably be two hours or more, and should most preferably be three hours or more.

The tearing strength of the porous sheet in accordance with the present invention should preferably be 180 gf/mm or higher, should more preferably be 250 gf/mm or higher, and should most preferably be 330 gf/mm or higher. The tensile strength at yield point should preferably be 110 kgf/cm$^2$ or higher, should more preferably be 120 kgf/cm$^2$ or higher, and should most preferably be 130 kgf/cm$^2$ or higher.

The porous sheet in accordance with the present invention is suitable for use as the backsheet of an absorbent article, such as a disposable diaper. Also, the porous sheet in accordance with the present invention may be laminated with woven fabrics, nonwoven fabrics, paper, or the like, and may thus be used as clothing and medical materials, such as waterproof materials, materials for protection against the cold, materials for protection against bacteria, tents, bedclothes, bandages, and base materials for cataplasms; packaging materials for keeping freshness, protecting the life of small animals, seeds, or the like, and preventing rottenness; materials for maturing fruits; light blocking materials; filtering materials; materials for separation films for preventing diffusion, and the like.

A process for producing the porous sheet in accordance with the present invention will be described hereinbelow.

In order for the porous sheet in accordance with the present invention to be produced, the melt mixture of the aforesaid resin composition is firstly molded to form a sheet. The aforesaid melt mixture is preferably obtained by kneading the aforesaid resin composition with a kneading technique utilizing an ordinary twin-screw kneading extruder. During the actual production, a method should preferably be employed, wherein the aforesaid crystalline polyolefin resin, and the fillers, the additives, and the like, which may be used when necessary, are supplied from a hopper by using a fixed displacement feeder, and the aforesaid compound is injected from a kneading region (i.e., a middle region) of the extruder, in which the resin has been plasticized, by using a fixed displacement pump. In cases where the lubricity of the fillers and the additives is high, they should preferably be dissolved or dispersed in the aforesaid compound and injected in this form by using the fixed displacement pump. In cases where the melting temperature of the aforesaid compound is equal to about room temperature (i.e., 19°–22° C.) or higher, the compound should preferably be heated to a temperature equal to its melting temperature or higher and injected in the liquid form.

In order for the sheet to be formed by carrying out the molding, a method should preferably be employed, wherein the aforesaid melt mixture is supplied to the die via a gear pump connected to the delivery region (i.e., the front end portion) of the twin-screw kneading extruder. Alternatively, a method should preferably be employed, wherein the twin-screw kneading extruder and a single-screw extruder are combined in series, and the aforesaid melt mixture is supplied to the die via the single-screw extruder.

It is also possible to employ a method, wherein the melt mixture is extruded to form filaments, the filaments are then cut in order to obtain pellets, and the obtained pellets are subjected to the molding step using a single-screw extruder provided with the die.

The molding step described above may be carried out by using either a flat die or a circular die. From the viewpoint of sheet yield, the circular die should preferably be used.

Thereafter, the sheet obtained from the molding step is stretched. The stretching step may be carried out with a monoaxial stretching method, wherein the sheet is stretched in the machine direction (MD). Alternatively, the stretching step may be carried out with a sequential biaxial stretching method, wherein the monoaxial stretching in the machine direction is followed by the stretching in the transverse direction (TD) using a tenter stretching machine, an air inflation stretching machine, a mandrel stretching machine, or the like. As another alternative, the stretching step may be carried out with a simultaneous biaxial stretching method, wherein the sheet is stretched simultaneously in the machine direction and the transverse direction. In general, the stretching temperature should preferably fall within the range of about room temperature (i.e., 19°–22° C.) to a temperature, which is lower by at least 10° C. than the melting temperature of the resin composition. The stretching temperature should more preferably fall within the range of about room temperature (i.e., 19°–22° C.) to a temperature, which is lower by at least 30° C. than the melting temperature of the resin composition. The stretch ratio of the length of the sheet after being stretched to the original length of the sheet should be at least 1.1:1.0 (i.e., the length of the sheet after being stretched is 1.1 when the original length of the sheet is taken as 1.0) in one direction. The stretch ratio should preferably be between 1.2:1.0 and 4.0:1.0, and should more preferably be between 1.3:1.0 and 3.0:1.0. Specifically, in the case of the monoaxial stretching, the stretch ratio in the machine direction should preferably be between 1.1:1.0 and 4.0:1.0. In the case of the biaxial stretching, each of the stretch ratio in the machine direction and the stretch ratio in the transverse direction should preferably be between 1.1:1.0 and 4.0:1.0. In such cases, good mechanical balance and a high strength can be kept, and good moisture permeability and good water pressure resistance can be obtained.

An embodiment of the absorbent article in accordance with the present invention will be described hereinbelow with reference to FIG. 1. The embodiment is constituted as a disposable diaper. The absorbent article in accordance with the present invention is also applicable to briefs for incontinent people, sanitary napkins, or the like.

Figure 1:
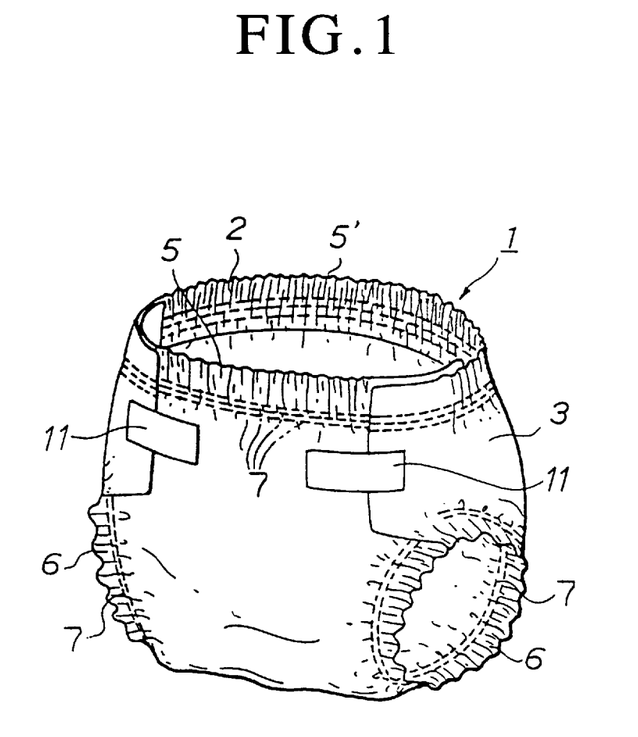
FIG. 1 is a perspective view showing an embodiment of the absorbent article in accordance with the present invention, which is constituted as a disposable diaper.

With reference to FIG. 1, a disposable diaper 1 serving as the absorbent article in accordance with the present invention comprises a liquid permeable topsheet 2, an antileakage backsheet 3, and an absorbent member (not shown) interposed between the topsheet 2 and the backsheet 3. The porous sheet in accordance with the present invention is employed as the backsheet 3.

Specifically, the disposable diaper 1 comprises the absorbent member for absorbing discharged liquids, such as urine, the topsheet 2 which covers the top surface of the absorbent member and which, in use, contacts the skin of the wearer, and the backsheet 3 which covers the back surface of the absorbent member and prevents liquid leakage. The absorbent member, the topsheet 2, and the backsheet 3 are adhered together into an integral body. The disposable diaper 1 is also provided with an elastic member 7, which prevents liquid leakage from an abdomen-side waist corresponding portions 5, a back-side waist corresponding portion 5', and a leg corresponding portion 6. The disposable diaper 1 is further provided with a securing tape 11 for securing the back-side waist corresponding portion 5' and the abdomen-side waist corresponding portion 5 to each other when the disposable diaper 1 is put on the wearer. For convenience, as the securing tape 11, a tape having a width of approximately 25 mm is used popularly.

The backsheet 3 comprises the porous sheet in accordance with the present invention. The thickness of the backsheet 3 should preferably be 25 to 55 $\mu$m, and should more preferably be 35 to 45 $\mu$m, from the viewpoint of the softness required for diapers, the stiffness of the sheet required during the assembling processing of the diapers, the feeling of safety by virtue of the presence of the backsheet, the softness required for the diapers, and the cost of the diapers.

The disposable diaper 1 as an embodiment of the absorbent article in accordance with the present invention is constituted in the manner described above. Ordinarily, in the disposable diaper having the structure described above, the strength of the backsheet required for a fastening tape to be directly adhered to and released from the backsheet, with a landing tape being omitted, is such that the tearing strength at the used sheet thickness may be 10 gf or higher, should preferably be 14 gf or higher, and should more preferably be 18 gf or higher. Therefore, for example, in order for a tearing strength of 10 gf to be obtained with the backsheet having a thickness of 55 $\mu$m, it is necessary that the tearing strength of the backsheet is 182 gf/mm. Also, the strength of the backsheet required for the fastening tape to be directly adhered to and released from the backsheet, with the landing tape being omitted, is such that the tensile strength at yield point may be 600 gf or higher per 1 cm of sheet width, should preferably be 700 gf or higher per 1 cm of sheet width, and should more preferably be 800 gf or higher per 1 cm of sheet width. Therefore, for example, in order for a tensile strength at yield point of 600 gf per 1 cm of sheet width to be obtained with the backsheet having a thickness of 55 $\mu$m, it is necessary that the tensile strength at yield point of the backsheet is 109 kgf/cm$^2$ or higher.

In the aforesaid disposable diaper as an embodiment of the absorbent article in accordance with the present invention, the porous sheet in accordance with the present invention is used as the backsheet. The tearing strength of the porous sheet is 180 gf/mm or higher, and the tensile strength at yield point thereof is 110 kgf/cm$^2$ or higher. Therefore, the backsheet has a sufficient strength. Thus with the absorbent article in accordance with the present invention, it is not necessary for the landing tape to be used. Accordingly, erroneous wearing of the diaper does not occur. Also, even if the securing tape is released for the purposes of investigating the urine discharge in use of the diaper, the backsheet does not break. Further, in cases where the moisture permeability of the backsheet falls within the range described above, stuffiness and other detrimental feelings do not occur, and a comfortable wearing feeling can be kept.

With the aforesaid porous sheet, it often occurs that the tensile yield point does not appear clearly, depending on the resin composition for the porous sheet. In such cases, the tensile stress at 100% elongation is employed as the tensile strength at yield point.

In the disposable diaper constituted in the manner described above, the strength of the backsheet required for the fastening tape to be directly adhered to and released from the backsheet, with the landing tape being omitted, is such that the tensile strength at yield point may be 600 gf or higher per 1 cm of sheet width, should preferably be 700 gf or higher per 1 cm of sheet width, and should more preferably be 800 gf or higher per 1 cm of sheet width. Therefore, for example, in order for a tensile strength at yield point of 600 gf per 1 cm of sheet width to be obtained with the backsheet having a thickness of 55 $\mu$m, it is necessary that the tensile strength at yield point of the backsheet is 109 kgf/cm$^2$ or higher.

As described above, with the backsheet of the aforesaid disposable diaper, the tensile strength at yield point of the backsheet is 110 kgf/cm$^2$ or higher, and thus the backsheet has a sufficient strength. Therefore, with the absorbent article in accordance with the present invention, it is not necessary for the landing tape to be used. Accordingly, erroneous wearing of the diaper does not occur. Also, even if the securing tape is released for the purposes of investigating the urine discharge in use of the diaper, the backsheet does not break. Further, in cases where the moisture permeability of the backsheet falls within the range described above, stuffiness and other detrimental feelings do not occur, and a comfortable wearing feeling can be kept.

In the present invention, it often occurs that the tensile yield point does not appear clearly, depending on the resin composition for the porous sheet. In such cases, the tensile stress at 100% elongation is employed as the tensile strength at yield point.

The present invention will further be illustrated by the following nonlimitative examples.

EXAMPLES 1 to 5, COMPARATIVE EXAMPLES 1 to 5

(Porous sheet)

Resin (1) and resin (2) described below were used as the crystalline polyolefin resin. Compound (1), compound (2) and compound (3) described below were used as the compound. Also, particulate material (1) and particulate material (2) described below were used as the particulate material. Resin compositions containing one of the crystalline polyolefin resins, one of the compounds, and one of the particulate materials in the proportions shown in Table 1 below were prepared. Each of the resin compositions thus obtained was molded with the molding method described below, and a sheet was thereby obtained. The compounds had the volatile temperatures and the melting temperatures listed in Table 2 below.

Resin (1): A resin obtained by blending, in a weight ratio of 1:1, a homopolypropylene resin (WT6048 supplied by Chisso Petrochemical Corporation), which had a density of 0.91 g/cm$^3$, a melt index of 0.4 g/10 min., and a melting temperature of 169° C., and an ethylene-propylene block copolymer resin (WT6052 supplied by Chisso Petrochemical Corporation), which had a density of 0.91 g/cm$^3$, a melt index of 0.5 g/10 min., a melting temperature of 168° C., and an ethylene content of 8% by weight.

Resin (2): An ethylene-propylene block copolymer resin (WT6052 supplied by Chisso Petrochemical Corporation), which had a density of 0.91 g/cm$^3$, a melt index of 0.5 g/10 min., a melting temperature of 168° C., and an ethylene content of 8% by weight.

Compound (1): An esterification product of trimethylolpropane and lauric acid (acid value=0.24, OH value=3.8; abbreviated to TTL)

Compound (2): A mineral oil (trade name "Diana Process Oil PW-90" supplied by Idemitsu Kosan K.K., flash temperature=272° C., aniline point=127.7° C., aromatics/naphthenes/paraffins ratio=0:29:71; abbreviated to PW-90)

Compound (3): A mineral oil (trade name "Ryupara 350S" supplied by Chuo Kasei K.K., flash temperature=220° C., aniline point=112° C., aromatics/naphthenes/paraffins ratio=0:34:66; abbreviated to 350S)

Particulate material (1): Calcium carbonate (trade name "Softon 2200" supplied by Bihoku Funka Kogyo K.K., average particle diameter=1 μm, maximum particle diameter=3 μm; abbreviated to CaCO$_3$)

Particulate material (2): Titanium oxide (trade name "Tipaque CR-60" supplied by Ishihara Sangyo Kaisha, Ltd., average particle diameter=0.2 μm, maximum particle diameter=0.35 μm; abbreviated to TiO$_2$)

TABLE 1

|  |  | Resin Composition (Parts by Weight) | | | | | |
|---|---|---|---|---|---|---|---|
|  |  | Resin | | Compound | | | Particulate Material |
|  |  | (1) | (2) | (1) | (2) | (3) | (1) | (2) |
| Examples | 1 | — | 75 | 25 | — | — | 15 | — |
|  | 2 | 75 | — | — | 25 | — | 25 | — |
|  | 3 | — | 82 | 18 | — | — | 20 | — |
|  | 4 | 80 | — | 20 | — | — | 35 | — |
|  | 5 | — | 88 | 12 | — | — | 25 | — |
| Comparative Examples | 1 | — | 70 | 30 | — | — | — | — |
|  | 2 | — | 72 | — | 27 | — | — | 2 |
|  | 3 | 73 | — | — | — | 27 | — | — |
|  | 4 | 70 | — | — | 30 | — | 50 | — |
|  | 5 | 60 | — | — | 40 | — | — | — |

TABLE 2

|  | Volatile Temperature (°C.) | Melting Temperature (°C.) |
|---|---|---|
| Compound (1) | 261 | 15 to 20 |
| Compound (2) | 244 | <0 |
| Compound (3) | 220 | <0 |

The volatile temperature was measured with SSC5000-TG/DTA200 supplied by Seiko Instruments Inc.

Molding method

A circular die (having a diameter of 200 mm) was connected to the front end (delivery opening) of a twin-screw kneading extruder (diameter=45 mm, L/D=33.5) with a gear pump interposed between them. Also, an air-cooled inflation molding equipment, in which the distance between the die and the nip roll was 4 m, was used. The crystalline polyolefin resin or a mixture, which was obtained by dry blending the crystalline polyolefin resin and the particulate material with a mixer, was supplied from a hopper. The compound having been heated and converted into the liquid form was injected with a gear pump into a middle region (i.e., a kneading region) of the twin-screw kneading extruder.

Temperatures were set to 190° C. at a cylinder C1 region (hopper side) of the extruder, 210° C. at a C2 region of the extruder, 220° C. at C3 through C8 regions, 230° C. at the gear pump region, and 220° C. at the die. While air having a temperature of 20° C. was being blown from an air ring to the blown film in order to effect forced air cooling, a sheet having a thickness of 38 to 40 μm was obtained at a sheet folding width of 60 cm and a take-off rate of 8 m/min.

The obtained sheet was then stretched according to the stretch processing method described below, and a porous sheet was thereby obtained.

Stretch processing method

With a roll stretching machine having a width of 1 m, the sheet was stretched in a stretch ratio of 1.5:1 in the molding direction at 50° C. Thereafter, the ultimate stretch ratio of 1.4:1 was obtained by carrying out an annealing step (i.e., the ultimate sheet length was 1.4 times as long as the original length of the sheet before being stretched). However, in each of Example 4 and Comparative Example 4, the sheet was stretched in a stretch ratio of 1.4:1 in the molding direction at 50° C., and thereafter the ultimate stretch ratio of 1.35:1 was obtained by carrying out an annealing step. Also, in each of Example 5 and Comparative Example 5, the sheet was stretched in a stretch ratio of 1.7:1 in the molding direction at 50° C., and thereafter the ultimate stretch ratio of 1.6:1 was obtained by carrying out an annealing step.

All of the thicknesses of the obtained sheets were 35 to 38 μm.

Rating criteria for porous sheet (i) Fuming during the molding; The fuming condition of a volatile matter during the sheet molding was visually investigated and rated on the scale described below.

Excellent: No fuming was observed.

Good: Slight fuming was observed.

Fair: Much fuming was observed.

Poor: Very much fuming was observed.

(ii) Time taken until occurrence (accumulation) of sticking of volatile matter; The time taken until a die line, which could be seen by the unaided eye, occurred on the sheet surface during the sheet molding was measured.

(iii) Sheet moldability; The sheet moldability was visually investigated and rated on the scale described below.

Excellent: The blown film was stable, and no die line was observed.

Good: The blown film was stable, but a die line was observed.

Fair: Fluctuations in the blown film occurred.

Poor: The molding was impossible.

(iv) Stretchability; In the stretch processing step, the sheet was visually investigated, and the stretchability was rated on the scale described below.

Excellent: No cutting and uniform whitening. (The inventors confirmed that there is correla tion between the whitening and the stretching.)

Good: No breakage, slight nonuniformity of whitening.

Fair: No breakage, much nonuniformity of whitening.

Poor: Breakage occurred.

(v) tensile strength at yield point; A testing sheet having a width of 10 mm was prepared and pulled at a rate of pulling of 300 mm/min. in the direction perpendicular to the stretching direction by using a Tensilon tensile tester. A stress/strain curve was drawn, and a stress peak point prior to the breakage was measured.

potassium sulfate, 0.010% of a Red No. 2 dye, 96.88% of water, and approximately 0.003% of polyoxyethylene nonyl phenol ether. The surface tension of the artificial urine was adjusted to be 50±1 dyne/cm.

TABLE 3

| | | Fuming during Molding | Time until Occurrence of Sticking of Volatile Matter (Hr) | Sheet Moldability | Stretchability | Feeling | Tensile Yield Strength *1) | Tearing Strength *2) | Moisture Permeability *3) | Water Pressure Resistance *4) | Anti-leakage Characteristics *5) |
|---|---|---|---|---|---|---|---|---|---|---|---|
| Examples | 1 | Excellent | >20 | Excellent | Excellent | Excellent | 121 | 340 | 2.1 | >2.0 | 2.0 |
| | 2 | Good | 10 | Excellent | Excellent | Excellent | 123 | 320 | 2.0 | >2.0 | 2.0 |
| | 3 | Excellent | >20 | Excellent | Excellent | Excellent | 131 | 410 | 1.8 | >2.0 | 3.0 |
| | 4 | Excellent | >20 | Excellent | Excellent | Excellent | 137 | 550 | 1.4 | >2.0 | 2.5 |
| | 5 | Excellent | >20 | Excellent | Excellent | Excellent | 134 | 320 | 1.6 | >2.0 | >3.0 |
| Comparative Examples | 1 | Excellent | >20 | Good | Good | Fair | 110 | 280 | 0.7 | >2.0 | 0.2 |
| | 2 | Good | 8 | Good | Fair | Fair | 111 | 290 | 0.4 | >2.0 | 0.4 |
| | 3 | Poor | 0.8 | Fair | Poor | Poor | 104 | 300 | 0.2 | >2.0 | 0.4 |
| | 4 | Good | 6 | Good | Fair | Poor | 97 | 205 | 1.1 | >2.0 | 0.2 |
| | 5 | Poor | 4 | Good | Good | Poor | 85 | 170 | 1.9 | >2.0 | <0.2 |

*1) (kgf/cm$^2$)
*2) (gf/mm)
*3) (g/100 cm$^2$ · Hr)
*4) (mAq)
*5) (Hr)

(vi) Tearing strength; A sample piece having a size of 30 mm width×60 mm length with respect to the stretching direction (i.e, the MD direction) was prepared. The sample piece was then cut over a length of 30 mm from the middle of the shorter side at an end with respect to the longitudinal direction to the interior in parallel with the longer side. Thereafter, the sample piece was set in a tensile tester such that the opposite sides of the shorter side having been cut might become the front and back faces. The sample piece was then torn at a rate of pulling of 300 mm/min., and the average stress was calculated.

(vii) Moisture permeability; The moisture permeability was measured according to the JIS Z0208 method.

(viii) Water pressure resistance; The water pressure resistance was measured according to the JIS L1093B method.

(ix) Feeling; The feeling of the sheet obtained from the stretch processing step was investigated by touching with fingers and rated on the scale described below.

Excellent: The sheet was soft and had a very good feeling.

Good: The sheet was soft and had a good feeling.

Fair: The sheet was slightly hard and had a slightly bad feeling.

Poor: The sheet was hard and had bad feeling. Or, the sheet was very sticky and had bad feeling.

(x) Antileakage characteristics; The sheet was placed horizontally, and 1 cc of artificial urine was placed on the upper surface of the sheet. A laboratory dish having a diameter of 10 cm and a height of 1 cm was then put over artificial urine on the upper surface of the sheet to prevent artificial urine from being volatilized. The time taken until the bleeding of artificial urine to the lower surface (the opposite surface) of the sheet could be seen by the unaided eye was measured. In cases where the measured time was three hours or longer, the antileakage characteristics were indicated as three hours or longer.

The aforesaid artificial urine used was prepared from 1.94% of urea, 0.795% of sodium chloride, 0.11% of magnesium sulfate, 0.062% of calcium chloride, 0.197% of EXAMPLES 6 and 7, COMPARATIVE EXAMPLES 6 and 7

(Absorbent article)

Disposable diapers, each of which was composed of a topsheet, an absorbent member, a backsheet, and securing tapes and had no landing tape, were produced. In Example 6, Example 7, Comparative Example 6, and Comparative Example 7, the porous sheet obtained in Example 1, the porous sheet obtained in Example 3, the porous sheet obtained in Comparative Example 2, and a porous sheet, which had been obtained from the conventional linear low-density polyethylene and calcium carbonate, were respectively used as the backsheet.

As a result, with the disposable diapers of Examples 6 and 7, the adhering and releasing of the fastening tape could be carried out more appropriately than the diaper of Comparative Example 7 using the conventional backsheet. Also, with the diaper of Comparative Example 6, in which the porous sheet of Comparative Example 2 was used, the adhering and releasing of the fastening tape could be carried out, but the moisture permeability was low, giving an unpleasant feeling to the wearer. In particular, with the diaper of Comparative Example 7, the fastening tape could not be released, and the backsheet was broken during the releasing of the fastening tape. As for the feeling, the diaper of Example 6 was soft and had the most excellent feeling.

What is claimed is:

1. A porous sheet formed from a melt mixture comprising:

(a) 100 parts by weight of a resin mixture consisting of 63 to 90 parts by weight of a crystalline polyolefin resin, and 37 to 10 parts by weight of a compound having a volatile of 240° C. or higher and a melting temperature of 90° C. or lower at ambient pressure; and (b) 7 to 40 parts by weight per 100 parts by weight of the resin mixture of a particulate material having an average particle diameter of 0.3 to 8 μm and a maximum particle diameter of 13 μm or smaller, the particulate material being not melted at a molding temperature of the resin mixture, said porous sheet formed by stretching in at least one direction; and said porous sheet having a moisture permeability of 0.5 to 4.0 q/100cm$^2$.hr as measured according to JIS Z 0208.

2. The porous sheet as claimed in claim 1, wherein the crystalline polyolefin resin is a polypropylene resin, a block copolymer of propylene and ethylene, or a mixture of the block copolymer and the polypropylene resin and/or a polyethylene resin.

3. An absorbent article comprising a liquid permeable topsheet, an antileakage backsheet, and an absorbent member interposed between the topsheet and the backsheet, wherein the backsheet comprises the porous sheet according to claim 2.

4. The porous sheet as claimed in claim 2, wherein the compound is a mineral oil or a compound having an ester bond in the molecule thereof.

5. An absorbent article comprising a liquid permeable topsheet, an antileakage backsheet, and an absorbent member interposed between the topsheet and the backsheet, wherein the backsheet comprises the porous sheet according to claim 4.

6. The porous sheet as claimed in claim 4, wherein the compound having an ester bond in the molecule thereof is an ester compound of a fatty carboxylic acid and a polyhydric alcohol.

7. The porous sheet as claimed in claim 1, wherein the compound is a mineral oil or a compound having an ester bond in the molecule thereof.

8. An absorbent article comprising a liquid permeable topsheet, an antileakage backsheet, and an absorbent member interposed between the topsheet and the backsheet, wherein the backsheet comprises the porous sheet according to claim 7.

9. The porous sheet as claimed in claim 7, wherein the compound having an ester bond in the molecule thereof is an ester compound of a fatty carboxylic acid and a polyhydric alcohol.

10. An absorbent article comprising a liquid permeable topsheet, an antileakage backsheet, and an absorbent member interposed between the topsheet and the backsheet, wherein the backsheet comprises the porous sheet according to claim 9.

11. The porous sheet as claimed in claim 1, wherein the particulate material is an inorganic particulate material.

12. An absorbent article comprising a liquid permeable topsheet, an antileakage backsheet, and an absorbent member interposed between the topsheet and the backsheet, wherein the backsheet comprises the porous sheet according to claim 11.

13. The porous sheet s claimed in claim 11, wherein the inorganic particulate material is calcium carbonate.

14. An absorbent article comprising a liquid permeable topsheet, an antileakage backsheet, and an absorbent member interposed between the topsheet and the backsheet, wherein the backsheet comprises the porous sheet according to claim 13.

15. An absorbent article comprising a liquid permeable topsheet, an antileakage backsheet, and an absorbent member interposed between the topsheet and the backsheet, wherein the backsheet comprises the porous sheet according to claim 1.

* * * * *